United States Patent [19]

Findeisen et al.

[11] Patent Number: 4,620,022

[45] Date of Patent: Oct. 28, 1986

[54] PREPARATION OF SUBSTITUTED TRIALKYLSILYLOXYMALONIC ACID DINITRILES

[75] Inventors: Kurt Findeisen, Odenthal; Rudolf Fauss, Cologne, both of Fed. Rep. of Germany

[73] Assignee: Bayer Aktiengesellschaft, Leverkusen, Fed. Rep. of Germany

[21] Appl. No.: 757,060

[22] Filed: Jul. 19, 1985

Related U.S. Application Data

[63] Continuation of Ser. No. 589,621, Mar. 14, 1984, abandoned.

[30] Foreign Application Priority Data

Mar. 25, 1983 [DE] Fed. Rep. of Germany ....... 3310954

[51] Int. Cl.$^4$ .............................................. C07F 7/10
[52] U.S. Cl. .................................................. 556/417
[58] Field of Search ......................................... 556/417

[56] References Cited

U.S. PATENT DOCUMENTS 4,430,503  2/1984  Findeisen ........................... 556/417

FOREIGN PATENT DOCUMENTS 0076985  4/1983  European Pat. Off. .
0076957  4/1983  European Pat. Off. .
2067211  7/1981  United Kingdom .

OTHER PUBLICATIONS

Chemische Berichte, vol. 106, 1973; W. Lidy et al, "Spaltungsreaktionen des Trimethylsilylcyanids . . . ", pp. 587–593.
Chemical Abstracts, vol. 79, No. 11, Sep. 17, 1973; W. Lidy et al, "Cleavage Reactions of Trimethylsilyl Cyanide . . . ", p. 460, p. 1, Abstract #66465t.
Lidy et al, Chem. Ber., vol. 106, pp. 587–593 (1973).
Lidy et al, Chemical Abstracts, vol. 79, 66465t (1973).
Hertenstein et al, Chem. Bur., vol. 115, pp., 263–287 (1982).

Primary Examiner—Dolph H. Torrence
Attorney, Agent, or Firm—Sprung Horn Kramer & Woods

[57] ABSTRACT

A process for the preparation of a substituted trialkylsilyloxymalonic acid dinitrile of the formula

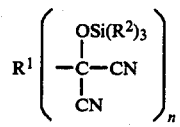

in which
R$^1$ is optionally substituted alkyl, optionally substituted cycloalkyl, optionally substituted aryl or optionally substituted heteroaryl,
R$^2$ is C$_{1-4}$-alkyl and
n is an integer from 1 to 4, comprising reacting a trialkylsilyl cyanide of the formula (R$^2$)$_3$SiCN with at least one acyl member selected from the group consisting of
(a) an acid halide of the formula

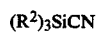

in which
Hal is fluorine, chlorine, bromine or iodine,
(b) an acyl cyanide of the formula

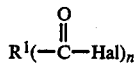

(c) a dimeric acyl cyanide or the formula

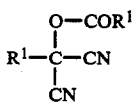

4 Claims, No Drawings

PREPARATION OF SUBSTITUTED TRIALKYLSILYLOXYMALONIC ACID DINITRILES

This is a continuation of application Ser. No. 589,621 filed Mar. 14, 1984 abandoned.

The present invention relates to processes for the preparation of substituted trialkylsilyloxymalonic acid dinitriles.

Trimethylsilyloxymalonic acid dinitriles and processes for their preparation are already known. Thus dicyano-trifluoromethyl-(trimethylsilyloxy)-methane is formed by reacting trifluoroacetyl chloride with 2 moles of trimethylsilyl cyanide. Other reactions described therein of acid chlorides with trimethylsilyl cyanide relate to phosgene and oxalyl chloride. The reaction of acid halides with trimethylsilyl cyanide accordingly seems restricted to very reactive acid chlorides (Chemische Berichte, Volume 106, pages 587–593, 1973).

However, it has been disclosed that less reactive acid chlorides, such as acetyl chloride and benzoyl chloride, can also be reacted with trimethylsilyl cyanide to give the corresponding trimethylsilyloxymalonic acid dinitriles. Nevertheless, the reaction is effected only at elevated temperature and with the addition of an extra catalyst (pyridine). Yields of up to 85% are achieved (Tetrahedron Letters No. 17, pages 1449 to 1450, 1973).

It was also known that 2-(trimethylsilyloxy)-2-propene nitriles are obtained when carboxylic acid chlorides are reacted with trimethylsilyl cyanide. It is furthermore known that the corresponding acyl cyanide is formed quantitatively when acid chlorides which contain a hydrogen atom in the β-position are reacted with trimethylsilyl cyanide in the presence of zinc iodide as the catalyst. This acyl cyanide can be converted into trimethylsilyloxymalonic acid dinitrile by reaction with further trimethylsilyl cyanide in the presence of tetrabutylammonium iodide. The same result is also obtained if the acid chloride is reacted with 2 moles of trimethylsilyl cyanide in the presence of tetrabutylammonium iodide. Trimethylsilyloxymalonic acid dinitrile can then be isolated in 78% yield (Chemische Berichte 115, 1982, pages 263–87).

The disadvantage of the known processes is that either only very reactive carboxylic acid halides can be reacted with trimethylsilyl cyanide, or the reaction must be carried out in the presence of expensive catalysts or at elevated temperatures and in the presence of catalysts.

It has been found that substituted trialkylsilyloxymalonic acid dinitriles of the general formula I

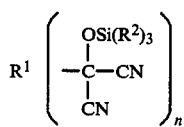

in which

R$^1$ represents optionally substituted alkyl, optionally substituted cycloalkyl, optionally substituted aryl or optionally substituted heteroaryl, R$^2$ represents C$_{1-4}$-alkyl and n represents an integer from 1 to 4, are obtained by a process in which (a) acid halides of the general formula II

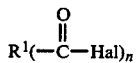

in which

R$^1$ and n have the abovementioned meaning and Hal represents fluorine, chlorine, bromine or iodine, are reacted with at least 2 moles of trialkylsilyl cyanide, per mole of the -COHal radical, of the formula III

in which

R$^2$ has the abovementioned meaning, the reaction being carried out, if appropriate, in the presence of acid or basic catalysts and the trialkylsilyl halide formed in the reaction continuously being removed from the reaction mixture, or (b) in which, in a first stage, the acid halide of the formula II is reacted with at least one molar equivalent of trialkylsilyl cyanide of the formula III per acid halide group at temperatures of 50° to 250° C., the trialkylsilyl halide formed is removed from the reaction mixture and the reaction mixture is then reacted with further trialkylsilyl cyanide of the formula III in the presence of a base at temperatures between −20° and +250° C., or (c) in which acyl cyanides of the general formula IV

in which

R$^1$ and n have the abovementioned meaning, are reacted with trialkylsilyl cyanide of the formula III, the reaction being carried out, if appropriate, in the presence of catalytic amounts of bases or acids at temperatures from −20° to +250° C., or (d) in the case where trialkylsilyloxymalonic acid dinitriles of the general formula I in which n represents 1 are to be obtained, in which dimeric acyl cyanides of the general formula V

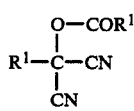

in which

R$^1$ has the abovementioned meaning, if appropriate as a mixture with acyl cyanides of the formula IV

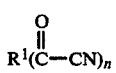

in which

R$^1$ has the abovementioned meaning and
n represents 1, are reacted with trialkylsilyl cyanides of the formula III, if appropriate in the presence of acids or bases at temperatures from −20 to +250° C.

The processes according to the invention for the preparation of the substituted trialkylsilyloxymalonic acid dinitriles of the general formula I differ from the known processes in that they are universally applicable, that is to say they are not restricted to reactive starting materials. Furthermore, they can be carried out without using expensive catalysts, such as tetrabutylammonium iodide, to give good yields. The substituted trialkylsilyloxymalonic acid dinitriles of the general formula I can thus be obtained less expensively and more easily with the aid of the processes according to the invention than with the known processes.

Compounds of the formula I which are preferably prepared by the processes according to the invention are those in which $R^1$ represents $C_{1-8}$-alkyl or $C_{3-12}$-cycloalkyl;

$C_{1-4}$-alkyl or $C_{3-6}$-cycloalkyl are particularly preferred. These radicals are optionally substituted by one or more identical or different radicals from the following group: halogen, in particular fluorine, chlorine or bromine, $C_{1-4}$-alkoxy, in particular methoxy or ethoxy, carboxyl, carbalkoxy, in particular methoxycarbonyl or ethoxycarbonyl, phenyl, phenoxy or henylthio it being possible for the phenyl rings to be substituted by halogen or alkyl; or $R^1$ furthermore represents phenyl or naphthyl, each of which can optionally be substituted by one or more identical or different radicals from the following group: halogen, in particular chlorine, bromine or fluorine, nitro, CN, $C_{1-4}$-alkyl, in particular methyl or ethyl, $C_{1-4}$-halogenoalkyl, in particular trifluoromethyl, trichloromethyl or pentafluoroethyl, $C_{1-4}$-alkoxy, in particular methoxy, ethoxy, $C_{1-4}$-halogenoalkoxy, in particular trifluoromethoxy, fluorochloromethoxy or pentafluoroethoxy, methylenedioxy, ethylenedioxy, difluoromethylenedioxy, chlorofluoroethylenedioxy, fluoroethylenedioxy, $C_{1-4}$-alkylthio, in particular methylmercapto, $C_{1-4}$-halogenoalkylthio, in particular trifluoromethylthio, $C_{2-8}$-alkoxyalkyl, in particular methoxymethyl, $C_{2-8}$-halogenoalkoxyalkyl, $C_{2-8}$-alkylmercaptoalkyl, in particular methylmercaptomethyl, $C_{1-4}$-alkylsulphonyl, in particular methylsulphonyl, $C_{1-4}$-halogenoalkylsulphonyl, carboxyl and carbalkoxy, in particular methoxycarbonyl or ethoxycarbonyl, or represents the radical $C_{1-4}$-alkoxy-N=CH—, in particular $CH_3$-O-N=CH-, or phenyl, phenoxy or thiophenyl, each of which can optionally be substituted by halogen or $C_{1-4}$-alkyl, or carboxyalkoxy with 2 to 4 C atoms, in particular carboxymethoxy, or $R^1$ furthermore represents heteroaryl, such as pyridinyl, pyrimidinyl, triazinyl, isoxazolyl, thiazolyl, oxadiazolyl, imidazolyl, triazolyl, furanyl, thiophenyl, each of which can optionally be mono- or poly-substituted by identical or different substituents from the group comprising halogen, in particular chlorine, $C_{1-4}$-alkyl, in particular methyl or ethyl and $C_{1-4}$-alkoxy, in particular methoxy or ethoxy, and can furthermore additionally be fused with one or more benzene rings.

Compounds of the formula I which are particularly preferably prepared by the processes according to the invention are those in which $R^1$ represents $C_{1-4}$-alkyl or halogen (in particular fluorine or chlorine), phenyl or phenoxy substituted $C_{1-4}$-alkyl or $C_{5-6}$-cycloalkyl, or represent phenyl, which is optionally substituted by halogen, in particular fluorine or chlorine, $C_{1-4}$-alkyl, in particular methyl, $C_{1-4}$-alkoxy, $C_{1-4}$-halogenoalkoxy, $C_{1-4}$-halogenoalkyl, $CH_3$O-N=CH- or nitro.

Compounds of the formula I which are very particularly preferably prepared are those in which $R^1$ represents phenyl which is optionally mono- or poly-substituted in the m,m' or p-positions by identical or different substituents from the group comprising chlorine, fluorine, methyl, methoxy, trifluoromethyl, trifluoromethoxy and bromine.

Acid halides of the formula II used as starting compounds in the processes according to the invention are known, and they can be prepared by known processes. The following acid halides are preferably used: acetyl chloride, propionyl chloride, pivaloyl chloride, cyclohexanecarboxylic acid chloride, benzoyl chloride, o-, m-, p-chlorobenzoyl chloride, 2,3-, 3,4-, 3,5-, 2,6-, 2,4-dichlorobenzoyl chloride, 2,3,4-, 2,3,5-, 3,4,5-trichlorobenzoyl chloride, naphthalene-1-carboxylic acid chloride, o-, m-, p-nitrobenzoyl chloride, o-, m-, p-trifluoromethylbenzoyl chloride, o-, m-, p-methoxybenzoyl chloride, 3,4-dimethoxybenzoyl chloride, o-, m-, p-trifluoromethoxybenzoyl chloride, o-, m-, p-fluorobenzoyl chloride, o-, m-, or p-bromobenzoyl bromide or chloride, 3-chloro-4-bromobenzoyl chloride, 3-bromo-4-chlorobenzoyl chloride, 3-chloro-4-methylbenzoyl chloride, 4-chloro-3-methylbenzoyl chloride, terephthalic acid dichloride, phthalic acid dichloride, tetrahydrophthalic acid dichloride, 4-chloro phthalic acid dichloride, pyromellitic acid tetrachloride, pyridine carboxylic acid chloride, thiophene-2-carboxylic acid chloride and 5-chlorothiophene-2-carboxylic acid chloride.

The trialkylsilyl cyanides used as starting compounds in the reactions according to the invention are known. Trimethylsilyl cyanide is preferably used. This can be obtained by reacting trimethylsilyl chloride with sodium cyanide (DE-OS (German Published Specification) 3,018,821, and EP-OS (European Published Specification) 40,356).

The silyl chlorides or bromides formed in the processes according to the invention can be converted back into the trialkylsilyl cyanides of the formula III by reaction with sodium cyanide.

Process a

If benzoyl chloride and trimethylsilyl cyanide are used as starting substances, the course of the reaction in process a can be represented by the following equation:

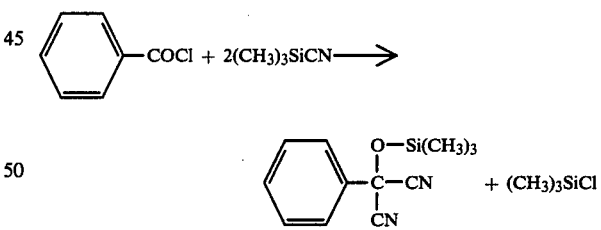

Process a is carried out by mixing the two reaction components and heating the mixture at the reflux temperature. The trialkylsilyl halide formed thereby distils off. However, the reaction can also be carried out by initially introducing one of the two reactants (preferably the acid halide) into the reaction vessel and adding the other reactant, with warming, at the rate at which the trialkylsilyl halide formed is removed by distillation. At least two equivalents of silyl cyanide are used per equivalent of acid halide radical. An excess of 0.05 to 2 moles of silyl cyanide may be advantageous. The rate of reaction can be favorably influenced by this excess, especially if no additional catalysts are used.

The reaction temperature can be varied within a substantial range. In general, it is between 0° and 250°

C., preferably between 30° and 200° and very particularly preferably between 60° and 150° C. The trimethylsilyl halide formed is preferably distilled off over a column either during the reaction or at the end of the reaction.

The reaction is in general carried out under normal pressure. If low-boiling aliphatic carboxylic acid chlorides are used, a slight increased pressure may be advantageous. The reaction is then carried out under 1 to 10 bar, preferably 1 to 5 bar. It may also be advantageous to carry out the reaction under reduced pressure, for complete removal of the trialkylsilyl halide formed.

Process variant a is preferably carried out without addition of further catalysts.

However, acid catalysts can also be used. Acid catalysts which may be mentioned are Lewis acids, such as aluminum chloride, iron-III chloride, antimony-V chloride, boron trifluoride, titanium-IV chloride, zinc chloride, tin-IV chloride, copper-I chloride, zinc iodide and mixtures of these compounds. Process a can also be carried out in the presence of basic catalysts. Preferred basic catalysts which may be mentioned are tertiary amines, alkali metal or alkaline earth metal hydroxides, alkali metal or alkaline earth metal carbonates, alkali metal or alkaline earth metal cyanides and alkali metal or alkaline earth metal salts of organic acids. The following basic catalysts may be mentioned as preferred: triethylamine, dimethylbenzylamine, pyridine, tetramethylethylenediamine, tributylamine, dimethylbutylamine, tetramethyl-1,3-butanediamine, hexamethylenediethylenetriamine, tetramethyl-1,2-propylenediamine, N-methylmorpholine, N,N'-dimethylpiperazine, N-methylpiperidine, tetramethylethylenediamine, 1-dimethylamino-3-formylaminopropane, quinoline, sodium hydroxide, potassium hydroxide, sodium cyanide, potassium cyanide, sodium carbonate, sodium acetate and mixtures of these compounds.

If sparingly soluble catalysts are used, such as, for example, sodium cyanide, it may be advantageous to add complexing agents or phase transfer catalysts, such as, for example, copper-I cyanide or crown ethers.

The feature of process a which is essential to the invention, that is to say the removal of the trialkylsilyl halide from the reaction mixture, is carried out either continuously during the reaction or at the end of the reaction. The end of the reaction can be detected by monitoring of the reaction mixture by IR spectroscopy (absence of the band in the C=O range of the IR spectrum). The reaction mixture is worked up by customary methods, for example by distillation. It may be advantageous to neutralize any basic catalysts present before carrying out the distillation, for example by addition of benzoyl chloride to the reaction mixture. For further processing of the substituted trialkylsilyloxymalonic acid dinitrile, it is frequently sufficient to distil off excess trialkylsilyl cyanide, after the trialkylsilyl halide formed has been distilled off either during or after the reaction, and to use the reaction mixture for further reactions.

The acid or basic catalysts used in the reaction are employed in amounts of 0.1 to 5% by weight, preferably 0.5 to 3% by weight, based on the acid halide used.

The reaction can be carried out in the presence of diluents which are inert towards the educts and products. Such diluents which may be mentioned are hydrocarbons, such as xylene and toluene, optionally substituted aromatics, such as chlorobenzene or nitrobenzene, tetramethylene sulphone and methylglutaric acid dinitrile. However, the reaction is preferably carried out without using diluents. Thus, for example, the starting components can be heated together, whereupon they melt when relatively high temperatures are reached and a homogeneous mixture forms.

Process b

Process b can be characterized by the following equation:

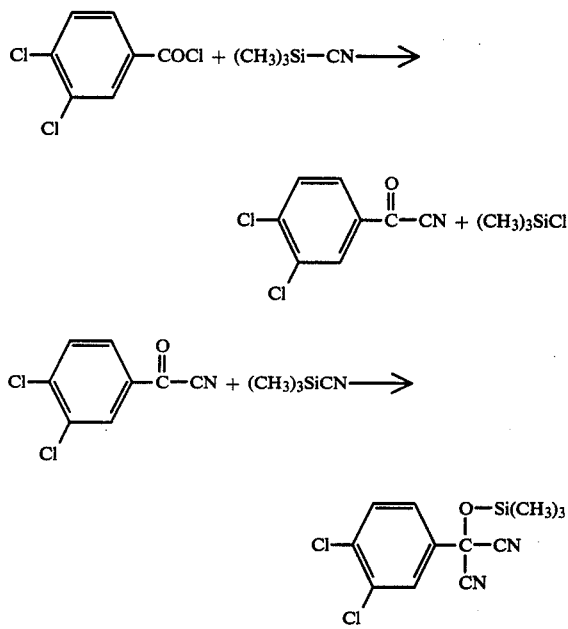

In process variant b, the acid halide is reacted completely with at least the equimolar amount of trialkylsilyl cyanide in a first stage. The silyl halide formed is thereby removed, preferably by distillation, either during the reaction or thereafter. Trialkylsilyl cyanide is then added to the reaction mixture, in the presence of catalytic amounts of base, in an amount that is together with the unreacted trialkylsilylcyanide from the first stage at least stoichiometrically sufficient.

The first stage of the reaction is carried out at temperatures from 0° to 250° C., preferably between 60° and 150° C. The second stage of the reaction is carried out at temperatures from −20° C. to +250° C., preferably at −10° to +60° and particularly preferably between +10° and +40° C. The basic catalysts mentioned for process a are used as basic catalysts in the second stage of process b.

Process b can be carried out in the presence of the solvents listed for process a. Process b is also preferably carried out without using diluents.

The second stage in process b can also be carried out by a procedure in which the product mixture obtained in the first stage, which, in addition to acyl cyanide, may also contain trialkylsilyl cyanide which has not yet reacted or a small amount of the substituted trialkylsilyloxymalonic acid dinitrile of the general formula I which has already formed, is added to a mixture of trialkylsilyl cyanide and catalytic amounts of a base.

The course of process b was surprising. Thus, it would have been expected that dimerization of the intermediately formed acyl cyanide, which readily proceeds in the presence of bases, leads to impurities (Angew. Chemie, Volume 68, page 434, 1956). It was also surprising that the second stage of the reaction proceeds rapidly and quantitatively at low temperatures and without addition of tributylammonium iodide.

The reaction mixture obtained after the second stage of process b can also be used directly for further reactions, if necessary after removal of excess silyl cyanide. If the reaction mixture is to be worked up by distillation, it is also advantageous to block the base by addition of, for example, benzoyl chloride for this operation.

Process c

If terephthalic acid dicyanide and trimethylsilyl cyanide are used as starting materials for process c, the course of the reaction can be represented by the following equation:

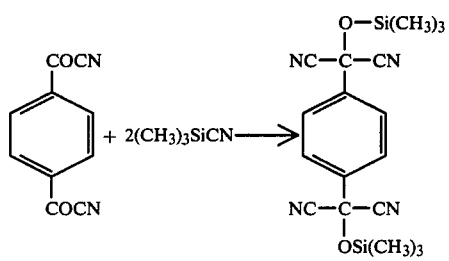

The acyl cyanides of the formula IV to be used as starting materials in process c are known, or they can be prepared by known processes. They can be obtained by reacting acid chlorides or acid anhydrides with alkali metal cyanides. Acyl cyanides of the formula IV which are derived from the acid halides listed under process a are preferably used in process c.

Process c is in general carried out without diluents. However, it can also be carried out with diluents which are inert towards the products and educts. Such diluents which may be mentioned are those listed under process a.

Process c can be carried out in the presence of acid or basic catalysts. Possible catalysts are the catalysts mentioned for process a. The catalysts are used in the same concentrations as indicated for process a. The reaction time and reaction temperature can be considerably reduced by addition of the catalysts.

The process is carried out between 0° and 250° C., preferably between 30° and 200° C. and very particularly preferably between 60° and 150° C.

The reaction conditions described under process b are particularly preferred for process c when carried out under basic catalysis. Thus, the base-catalyzed reaction preferably proceeds at temperatures from 10° to 40° C.

Acyl cyanides and trialkylsilyl cyanides are brought together in the stoichiometric ratio in the the catalyzed reaction. A slight excess of trialkylsilyl cyanide may be advantageous. If no catalyst is used, it is advantageous to carry out the reaction at high temperatures and with an excess of 5 to 100 mole % of trialkylsilyl cyanide.

The reaction components are brought together in any desired sequence in process c. Thus, the catalyst can be added with one of the two reaction components to the other component. However, it can also be mixed with the two reaction components. In the case of acyl cyanides which readily dimerize, such as, in particular, aliphatic acyl cyanides, the basic catalyst is preferably initially introduced into the reaction vessel with the trialkylsilyl cyanide and the acyl cyanide is added to this mixture.

Process c is in general carried out under normal pressure. It may be advantageous to allow the reaction to proceed under a slight increased or reduced pressure.

Process c is particularly preferably carried out at temperatures between 10° and 40° C. in the presence of basic catalysts. Particularly preferred basic catalysts here are the tertiary amines listed for process a.

Process d

If dimeric pivaloyl cyanide and trimethylsilyl cyanide are used as starting materials for process d, the course of the reaction can be represented by the following equation:

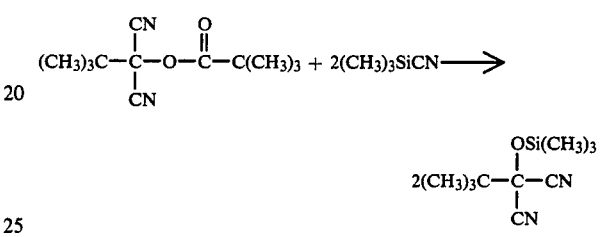

Formula V provides a general definition of the dimeric acyl cyanides used in process d. These are known compounds, which can be prepared by known processes (Angew. Chemie, Volume 94, page 13, 1982). The dimeric acyl cyanides of the formula V which are derived from the carboxylic acid halides listed for process a are preferably used in process d. Compounds of the formula V in which $R^1$ represents optionally substituted $C_{1-8}$-alkyl are particularly preferred here.

The dimeric acyl cyanides of the formula V frequently form during the preparation of the monomeric acyl cyanides of the formula IV, which are therefore often contaminated with these dimeric acyl cyanides. It is a particular advantage of process d that these dimeric acyl cyanides, which may, where relevant, be present as a mixture with the monomeric acyl cyanides, can also be converted into the desired substituted trialkylsilyloxymalonic dinitriles of the general formula I without expensive separation.

Process d is preferably carried out in the presence of acid or basic catalysts. Possible catalysts are the basic and acid catalysts mentioned for process a. However, the process can also be carried out without using catalysts.

If no catalysts or acid catalysts are used, the process is carried out at temperatures from −20° to +250° C., preferably between 80° and 200° C.

If process d is carried out in the presence of basic catalysts, the preferred temperature is between 0° and 70° C., preferably room temperature.

The dimeric acyl cyanides of the formula V and the trialkylsilyl cyanides of the formula III are used in the stoichiometric amounts in process d. An excess of trialkylsilyl cyanide of 10 to 200 mole % may be advantageous.

Process d can be carried out in the presence of diluents which are inert towards the educts and products. Diluents which may be mentioned are those listed for process a. However, the procedure in the absence of diluents is particularly preferred. If the educts are solid at the start of the reaction, a homogeneous solution can also be achieved, without addition of diluents, by mixing the educts and, if appropriate, warming the mixture slightly. Process d is preferably carried out under normal pressure. However, it can also be carried out under an increased pressure of 1 to 10 bar.

After the reaction has been carried out, any excess of the silyl cyanide is removed by distillation. The reaction mixture can usually be used for the secondary reaction, without further working up.

As already mentioned, process d is particularly preferably carried out under basic catalysis. The reaction thereby proceeds virtually quantitatively.

The substituted trialkylsilyloxymalonic acid dinitriles of the formula I prepared according to processes a–d are important starting materials for the preparation of insecticidal and acaricidal active compounds. Thus, they can be used for the preparation of the compounds known from DE-OS (German Published Specification) 3,140,275.

The examples which follow illustrate the present invention, without indicating a restriction in respect of its feasibility.

EXAMPLE 1

(process a)

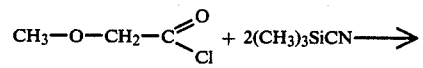

593 g of 2-chlorobenzoyl chloride and 2 g of zinc chloride were heated to 120°–140° C., 693 g of trimethylsilyl cyanide were added dropwise and the trimethylsilyl chloride simultaneously formed was distilled off over a short column. Towards the end of the distillation, the bottom temperature was increased to 180°–190° C. and was kept at this level for 1 hour. The crude product was distilled. 425 g of pure o-chlorophenyltrimethylsilyloxymalonic acid dinitrile of boiling point $_{0.3}$106°–109° C. were obtained.

In addition to the desired product, the first runnings also contained o-chlorobenzoyl cyanide.

The following compounds were prepared analogously to Example 1:

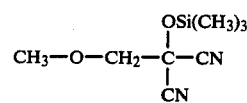

| 2. | OSi(CH$_3$)$_3$<br>C—CN<br>CN (naphthyl) | Boiling point:<br>155–60° C./0.5 mm hg |
|---|---|---|
| 3. | OSi(CH$_3$)$_3$<br>C—CN<br>CN (cyclohexyl, H) | Crude product, distills only with decomposition |
| 4. | 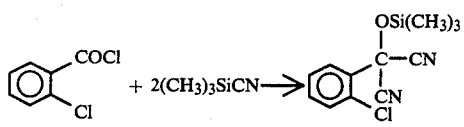 | 136–138° C./12 mm hg |

EXAMPLE 5

(process a)

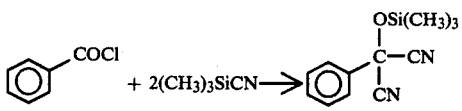

105 g of methoxyacetyl chloride and 192 g of trimethylsilyl cyanide were stirred at 80°–90° C. for 30 minutes and the temperature was then slowly increased to 130° C. and the trimethylsilyl chloride was simultaneously distilled off over a short column. The crude product was then distilled.

125 g of methoxymethyltrimethylsilyloxymalonic acid dinitrile were obtained. Boiling point $_{16}$:98°–100° C.

EXAMPLE 6

(process a)

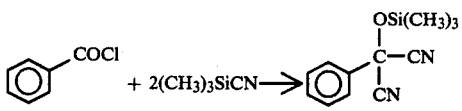

281 g of benzoyl chloride and 218 g of trimethylsilyl cyanide were heated and the trimethylsilyl chloride formed was distilled off over a 40 m Vigreux column.

Towards the end of the distillation, a further 200 g of trimethylsilyl cyanide were added and the mixture was heated under reflux at about 150° C. for 3 hours. It was then subjected to incipient distillation. 475 g of phenyltrimethylsilyloxymalonic acid dinitrile (gas chromatography: 96%) remained as the bottom product.

EXAMPLE 7

(process b)

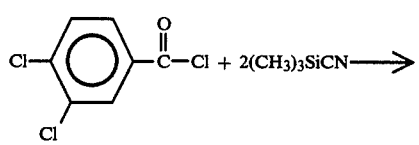

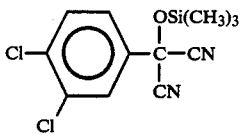

416 g of trimethylsilyl cyanide were added to 852 g of 3,4-dichlorobenzoyl chloride at 80°–90° C. and the trimethylsilyl chloride formed on further heating was distilled off over a 20 cm Vigreux column. After the bottom temperature had risen to 120° C., a further 100 g of trimethylsilyl cyanide were added. When no further acid chloride remained in the bottom product (checked by IR spectroscopy), the mixture was cooled, 2 ml of triethylamine were added at 20° C. and a further 320 g of trimethylsilyl cyanide were added dropwise, with cooling. The mixture was subsequently stirred at room temperature for 1 hour and checked by IR spectroscopy to ensure that the carbonyl band no longer appeared. After stabilization with 3 ml of benzoyl chloride, the product was subjected to incipient distillation.

1,190 g of residue remained, which, according to gas chromatography, consisted of 98% of 3,4-dichlorophenyl-trimethylsilyloxymalonic acid of dinitrile. Distillation gave 1,130 g of pure substance. Boiling point: 114°–117° C./0.15 mm hg.

EXAMPLE 8

(process c)

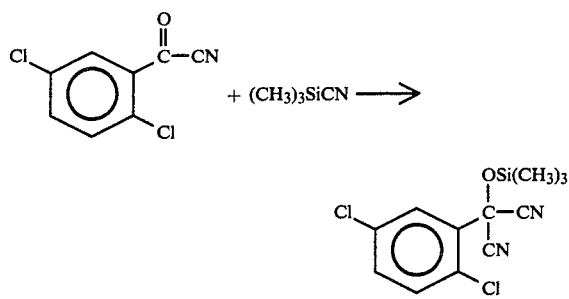

40 g of 2,5-dichlorobenzoyl cyanide and 20 g of trimethylsilyl cyanide were heated to 195° C. in the course of 2 hours and stirred for 2 hours.

Distillation gave 39.5 g of 2,5-dichlorophenyltrimethylsilyloxymalonic acid dinitrile of boiling point 0.2 113°–116° C. and melting point 62°–64° C.

The following compounds were prepared analogously to Example 8:

|    |                                                                                  | Boiling point        |
|----|----------------------------------------------------------------------------------|----------------------|
| 9. | F—CH$_2$—C(CH$_3$)(CH$_3$)—C(OSi(CH$_3$)$_3$)(CN)—CN                             | 90–93° C./12 mm hg   |
| 10.| CH$_3$—C(CH$_3$)(CH$_3$)—C(OSi(CH$_3$)$_3$)(CN)—CN                               | 75–77° C./12 mm hg   |

EXAMPLE 11

(process c)

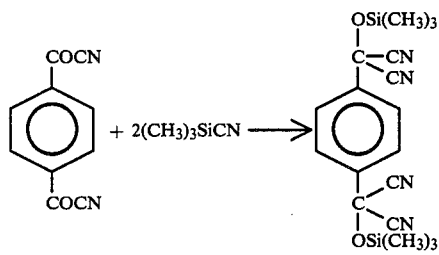

73.6 g of terephthalic acid dicyanide and 190 g of trimethylsilyl cyanide were slowly warmed to 160° C. with 1 g of zinc chloride. After 1 hour, the reaction had ended and excess trimethylsilyl cyanide was distilled off in vacuo. Spectroscopy data showed the presence of the desired substance, which it was not possible to distill without decomposition.

According to Example 11

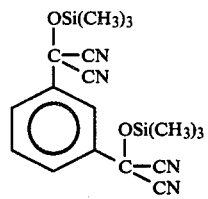

was synthesized; the substance cannot be distilled.

EXAMPLE 13

(process c)

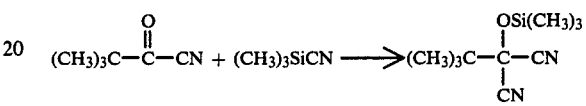

149 g of trimethylsilyl cyanide and 1 ml of triethylamine were initially introduced into the reaction vessel and 190 ml of pivaloyl cyanide were added dropwise at a maximum of 40° C., while cooling with ice. The mixture was then distilled under a water pump vacuum. It was possible to obtain 293 g of t-butyltrimethylsilyloxymalonic acid dinitrile. Boiling point 14:77° C.

EXAMPLE 14

(process c)

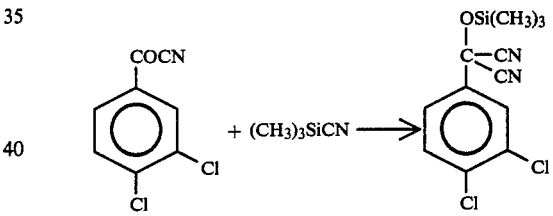

200 g of trimethylsilyl cyanide were added to 400 g of 3,4-dichlorobenzoyl cyanide and 1.5 ml of triethylamine at a maximum of 30° C. The mixture was subsequently stirred for 1 hour; the carbonyl band had disappeared from the IR spectrum. According to investigation by spectroscopy, the residue consisted of 3,4-dichlorophenyltrimethylsilyloxymalonic acid dinitrile.

Hydrolysis of the product in concentrated sulphuric acid gave 3,4-dichlorophenylhydroxymalonic acid diamide.

EXAMPLE 15

(process c)

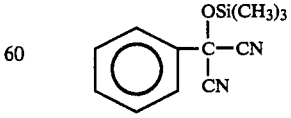

0.3 g of sodium cyanide and 0.1 g of copper-I cyanide were added to 131 g of benzoyl cyanide. 105 g of trimethylsilyl cyanide were added dropwise at a maximum of 40° C. The mixture was subsequently stirred at 40° C. for 4 hours. The C=O band was no longer visible in the IR spectrum. After the slight excess of trimethylsilyl cyanide had been distilled off, 215 g of phenyltrimethylsilyloxymalonic acid dinitrile remained as the residue.

EXAMPLE 16

(process d)

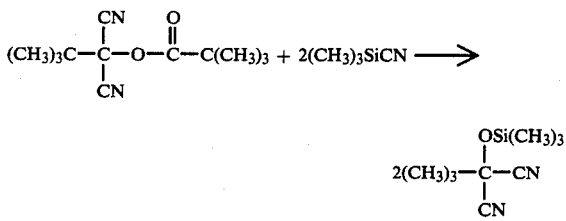

0.4 ml of triethylamine was added to 31 g of dimeric pivaloyl cyanide and 30 g of trimethylsilyl cyanide at room temperature and the solution was stirred for 4 hours. The carbonyl band was no longer to be seen in the IR spectrum.

According to investigation by gas chromatography against a comparison substance, tert.-butyltrimethylsilyloxymalonic acid dinitrile had formed.

EXAMPLE 17

(process d)

111 g of dimeric pivaloyl cyanide and 55 g of trimethylsilyl cyanide were heated to 190° C. and a further 55 g of trimethylsilyl cyanide were then slowly added dropwise. The bottom temperature thereby dropped to 153° C. The mixture was then distilled. In addition to a little starting product, 150 g of tert.-butyltrimethylsilyloxymalonic acid dinitrile were obtained. Boiling point $_{14}$:77°–78° C.

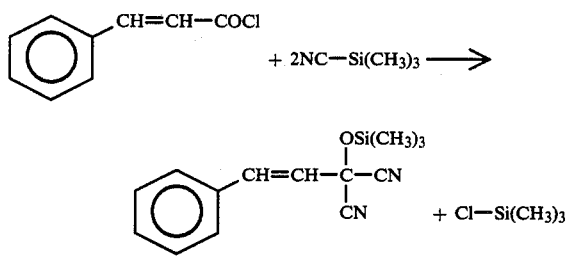

33,3 g (o,2 mol) of cinnamic chloride and 99 g (1 mol) of trimethylsilyl cyanide were mixed with DABCO (2,2,2-diazabicyclooctane) at room temperature. After about 2 minutes an exothermic reaction began during which the temperature rose to 48° C. The mixture was then subsequently stirred for 30 minutes at 50° C. The trimethylsilyl chloride formed and the excess trimethylsilyl cyanide were distilled in a water-jet vacuum at 50° C. 42 g of Styryltrimethylsilyloxymalonic acid dinitrile remained.

The use of DABCO is particularly advantageous in carrying out processes a–d of the invention. It allows the process to be carried out at lower temperatures. In this way sensitive starting compounds can also be reacted. It will be appreciated that the instant specification and examples are set forth by way of illustration and not limitation, and that various modifications and changes may be made without departing from the spirit and scope of the present invention.

We claim:

1. A process for the preparation of a substituted trimethylsilyloxymalonic acid dinitrile of the formula

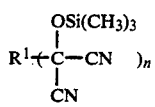

in which

R$^1$ is phenyl, or phenyl substituted in at least one of m-,m'-, and p-positions by chlorine, fluorine, methyl, methoxy, trifluoromethyl, trifluoromethoxy or, bromine, and n is an integer from 1 to 4, which comprises in a first step reacting an acid halide of the formula

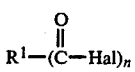

in which

Hal is fluorine, chlorine, bromine or iodine, with at least its molar equivalent amount per acid halide substituent of trimethylsilylcyanide of the formula

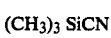

at a temperature between 60° and 150° C., removing the by-product trialkylsilylhalide, and reacting the reaction mixture with additional trimethylsilylcyanide in the presence of a base at a temperature between −10° and +60° C.

2. A process for the preparation of a substituted trimethylsilyloxymalonic acid dinitrile of the formula

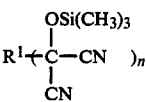

in which

R$^1$ is phenyl, or phenyl substituted in at least one of m-,m'-, and p-positions by chlorine, fluorine, methyl, methoxy, trifluoromethyl, trifluoromethoxy or, bromine, and n is an integer from 1 to 4, which comprises reacting an acylcyanide of the formula

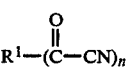

with trimethylsilylcyanide of the formula

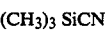

in the presence of a catalytic amount of a base at a temperature between −10° and +60° C.

3. A process for the production of a substituted trimethylsilyloxymalonic acid dinitrile of the formula

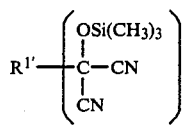

in which $R^{1'}$ is $C_1$–$C_8$-alkyl, or $C_1$–$C_8$-alkyl substituted by halogen and/or $C_1$–$C_4$-alkoxy, which comprises reacting a dimeric acylcyanide of the formula

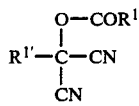

in which $R^1$ is phenyl, or phenyl substituted in at least one of m-, m'-, and p-positions by chlorine, fluorine methyl, methoxy trifluoromethyl, trifluorometoxy or, bromine, with trimethylsilylcyanide of the formula

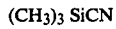

in the presence of a catalytic amount of a base at a temperature between 0° and 70° C.

4. A process according to claim 3, wherein the dimeric acylcyanide undergoing reaction is admixed with acylcyanide of the formula

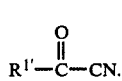

* * * * *

UNITED STATES PATENT AND TRADEMARK OFFICE
CERTIFICATE OF CORRECTION

PATENT NO. : 4,620,022
DATED : October 28, 1986
INVENTOR(S) : Kurt Findeisen, et al.

It is certified that error appears in the above-identified patent and that said Letters Patent are hereby corrected as shown below:

Title Page, under "Other Publications", line 10     Delete "Bur." and substitute --Ber.--

Col. 3, line 18     Delete "henylthio" and substitute --phenylthio--

Col. 10, line 1     Delete "136°-138° C./12 mm hg"

Col. 12, line 5     Insert --12.--

Col. 13, line 38     Insert --EXAMPLE 18 (process a)--

Signed and Sealed this

Twenty-fourth Day of March, 1987

Attest:

DONALD J. QUIGG

Attesting Officer     Commissioner of Patents and Trademarks